United States Patent
Hong et al.

(10) Patent No.: US 11,273,194 B2
(45) Date of Patent: Mar. 15, 2022

(54) PHARMACEUTICAL COMPOSITION CONTAINING AVOCADO OIL FRACTION AS ACTIVE INGREDIENT FOR PREVENTION OR TREATMENT OF HEARING LOSS

(71) Applicant: DONG KOOK PHARM CO., LTD, Seoul (KR)

(72) Inventors: Bin Na Hong, Gyeonggi-do (KR); Woo Jae Jung, Seoul (KR); Kye Wan Lee, Seoul (KR); Jung Suk Lee, Seoul (KR); Yu Hwa Park, Gyeonggi-do (KR); Do Hoon Kim, Incheon (KR)

(73) Assignee: DONG KOOK PHARM CO., LTD, Seoul (KR)

(*) Notice: Subject to any disclaimer, the term of this patent is extended or adjusted under 35 U.S.C. 154(b) by 132 days.

(21) Appl. No.: 16/791,570

(22) Filed: Feb. 14, 2020

(65) Prior Publication Data
US 2020/0215142 A1   Jul. 9, 2020

Related U.S. Application Data (63) Continuation-in-part of application No. PCT/KR2018/010513, filed on Sep. 7, 2018.

(30) Foreign Application Priority Data

Sep. 8, 2017  (KR) ........................ 10-2017-0115414

(51) Int. Cl.
*A61K 36/54* (2006.01)
*A61P 27/16* (2006.01)

(52) U.S. Cl.
CPC .............. *A61K 36/54* (2013.01); *A61P 27/16* (2018.01); *A61K 2236/333* (2013.01); *A61K 2236/39* (2013.01)

(58) Field of Classification Search
None
See application file for complete search history.

(56) References Cited

U.S. PATENT DOCUMENTS

| | | | |
|---|---|---|---|
| 6,552,208 | B1 | 4/2003 | Alander et al. |
| 2004/0235803 | A1* | 11/2004 | Britten ............. A61P 15/14 514/165 |
| 2010/0035816 | A1 | 2/2010 | Piccirilli et al. |
| 2011/0082070 | A1 | 4/2011 | Piccirilli et al. |

FOREIGN PATENT DOCUMENTS

| | | | | |
|---|---|---|---|---|
| FR | 2778181 | A1 * | 11/1999 | ........... C07D 307/36 |
| JP | 2011-37738 | A | 2/2011 | |
| JP | 2011037738 | A * | 2/2011 | |
| KR | 10-2009-0119020 | | 11/2009 | |
| WO | WO 1999/55657 | | 11/1999 | |

OTHER PUBLICATIONS

Costagli (Journal of Agricultural Engineering (2015) XLVI:467, pp. 115-112).*
Lozano et al., "Unsaponifiable matter, total sterol and tocopherol contents of avocado oil varieties," *Journal of American Oil Chemists' Society* 70(6): 561-565 (Jun. 1993).
International Search Report from parent PCT Application No. PCT/KR2018/010513, 3 pages (dated Mar. 14, 2019).

* cited by examiner

*Primary Examiner* — Susan Hoffman
(74) *Attorney, Agent, or Firm* — Klarquist Sparkman, LLP (57) ABSTRACT

The present invention relates to a pharmaceutical composition containing an avocado oil fraction as an active ingredient for prevention or treatment of hearing loss. Specifically, the avocado oil fraction according to the present invention, especially an isopropanol fraction of avocado oil significantly increases the number of hair cells reduced by neomycin in zebrafish models, so the isopropanol fraction of avocado oil can be favorably used in the treatment of hearing loss.

4 Claims, 11 Drawing Sheets

Normal  Control  Avocado oil  Isopropanol fraction of avocado oil (HP-20)

NOR:Normal
NM:Control
LA:Linoleic acid
AL:α-Linoleic acid
ST:Stearic acid

Figure 8

NOR:Normal
NM:Control
LA:Linoleic acid
AL:α-Linoleic acid
ST:Stearic acid

PHARMACEUTICAL COMPOSITION CONTAINING AVOCADO OIL FRACTION AS ACTIVE INGREDIENT FOR PREVENTION OR TREATMENT OF HEARING LOSS

CROSS REFERENCE TO RELATED APPLICATION

This is a continuation-in-part of PCT/KR2018/010513, filed Sep. 7, 2018, which claims priority to Korean Patent Application No. 10-2017-0115414, filed on Sep. 8, 2017. The contents of the prior applications are incorporated herein by reference in their entirety.

BACKGROUND OF THE INVENTION

1. Field of the Invention

The present invention relates to a pharmaceutical composition containing an avocado oil fraction as an active ingredient for prevention or treatment of hearing loss.

2. Description of the Related Art

The ear is divided into three parts, the outer ear (pinna and external ear canal), the middle ear (tympanic membrane and auditory ossicles) and the inner ear (cochlea and auditory nerve).

Sound is acoustic energy transmitted through the pinna and the external ear canal to vibrate the tympanic membrane, and the vibration of the tympanic membrane generates mechanical energy and this is transmitted to the auditory ossicles. The stapes, the last bone of the auditory ossicles, is connected to the cochlea, which transfers the energy delivered to lymph in the cochlea. The energy delivered to the lymph causes waves in the lymph, which stimulates the hair cells in the cochlea. As the movement of the hair cells causes ion changes, neurotransmitters are delivered to the auditory nerve attached to the hair cells, and sound energy is transmitted from the auditory nerve to the brain in the form of electric energy.

The outer ear and the middle ear are sound-transmitting organs. When these organs are infected with a disease such as inflammation, most of them can be recovered by treatment or surgery, and the resulting hearing loss can also be ameliorated by treatment. This hearing loss is called conductive hearing loss. On the other hand, the hearing loss caused by problems in the cochlea which is the sound-sensing organ, the auditory nerve that delivers sound through electrical energy, and the brain which plays a comprehensive role such as sound distinction and understanding, is called sensorineural hearing loss.

Among the sensory organs of the body, the auditory organ is the most basic sensory organ for communication, and it is one of the most important sensory organs for acquiring language or knowledge, social life, and human life. Most hearing loss is the sensory neurological hearing loss that has no treatment other than prevention until now. Once the hearing loss occurs, treatment can be done by using an aid such as a hearing aid or by implanting a mechanical device into the body. The sensorineural hearing loss can be categorized according to the cause and time of the onset. Depending on the time, it is classified as innate hearing loss and acquired hearing loss. The innate hearing loss is a hearing loss caused by injury before birth, which is caused by problems in heredity, the womb or the birth process.

The innate hearing loss is usually very severe and language acquisition is impossible without additional training or education. In order to treat the innate hearing loss, a high-powered hearing aid or a cochlear implant is implanted to hear the sound. However, such auxiliary device is less effective as the degree of hearing loss increases, and the listening ability of such device differs from the normal listening ability, which makes daily life still inconvenient. On the other hand, the acquired hearing loss is a hearing loss caused by a disease, noise, drugs or accidents after birth, and the causative factors include noise, drugs, aging, trauma, and viruses. Recently, hearing loss due to noise and aging has been increasing rapidly.

As the life of human beings is prolonged by the development of science and technology, the elderly population is rapidly increasing all over the world. Most age-related hearing loss is also sensorineural hearing loss, and there are no drugs or treatments for treatment or amelioration other than prevention and management.

In addition, due to the industrialization of society, noise-induced hearing loss is also increasing rapidly. In addition to occupational noise-induced hearing loss developed in workers or soldiers working in a noisy environment, noise-induced hearing loss due to cultural and leisure life is also increasing. In this regard, OSHA (Occupational Safety and Health Administration) in the United States implements noise management for noisy environments above 85 dBA. Studies have reported that the human auditory organs are affected by noise above 75 dBA. Since the noise of 75 dBA is the noise of roadsides, it can be said that everyone lives in a noise that is harmful to auditory organs in modern society. In addition, in the leisure life such as the use of MP3 is often exposed to loud sound, noise-induced hearing loss occurs at various age groups.

The noise-induced hearing loss that occurred in younger years damages hearing ability to the extent that hearing aids should be used from those in their 40s, and the level of hearing loss increases when physical aging is combined. Since the effect of hearing aids also decreases as the degree of hearing loss increases, high-level hearing loss eventually leads to serious problems in communication.

In this regard, Korean Patent Application No. 10-2008-0044810 discloses that Scutellaria radix extract has a significant effect on preventing hearing loss in a noise-induced hearing loss animal model. In addition, as an effective substance for preventing or treating hearing loss, antioxidants, NMDA (N-methyl-D-aspartate) antagonists, apoptosis inhibitors, growth factors, and the like have been studied. However, these substances have shown limited progress in clinical trials.

Thus, while developing a substance that can be used to treat hearing loss, the present inventors completed this invention by confirming that the isopropanol fraction eluted by adsorption chromatography using avocado oil significantly increased the number of hair cells reduced by neomycin in the zebrafish model.

SUMMARY OF THE INVENTION

It is an object of the present invention to provide a composition for the treatment of hearing loss comprising an avocado oil fraction.

To achieve the above object, the present invention provides a pharmaceutical composition containing an isopropanol fraction of avocado oil as an active ingredient for the prevention or treatment of hearing loss.

The present invention also provides a health functional food containing an isopropanol fraction of avocado oil as an active ingredient for the amelioration of hearing loss.

The present invention also provides a method for preventing, ameliorating or treating hearing loss, comprising the step of administering an isopropanol fraction of avocado oil to a subject.

In addition, the present invention provides a use of avocado oil for the preparation of a medicament for the prevention, amelioration or treatment of hearing loss.

Advantageous Effect

The avocado oil fraction according to the present invention, especially, an isopropanol fraction of avocado oil significantly increases the number of hair cells reduced by neomycin in zebrafish models, so the isopropanol fraction of avocado oil can be favorably used in the treatment of hearing loss.

DESCRIPTION OF THE PREFERRED EMBODIMENTS

Hereinafter, the present invention is described in detail.

The present invention provides a pharmaceutical composition containing an isopropanol fraction of avocado oil as an active ingredient for the prevention or treatment of hearing loss.

The term used in this specification "avocado oil" refers to an aromatic component extracted from avocado by compression, leaching, distillation, and the like. The said avocado oil can be used as avocado essence, perfume oil, essential oil and refined oil.

The avocado oil can be the oil extracted from any one or more selected from the group consisting of peel, pulp and seeds of avocado, and the oil extracted from peel and pulp of avocado by pressing. It can be extracted by compression, solvent extraction, supercritical carbon dioxide extraction or steam distillation.

The term used in this specification "fraction" refers to a liquid obtained by adsorbing a sample on a chromatography filled with a specific resin and then adding an eluting solvent. That is, the isopropanol fraction of avocado oil according to the present invention can be obtained by adsorbing avocado oil on a chromatography filled with a resin for adsorption chromatography, and then sequentially adding water, ethanol and isopropanol as eluting solvents. The eluting solvent can be used at 45~85° C., specifically 50~80° C., and more specifically 55~75° C.

The resin for adsorption chromatography can be silica gel or synthetic adsorbent. The synthetic adsorbent can be composed of a copolymer, and the copolymer can be a copolymer of styrene and divinylbenzene (DVB).

The hearing loss can be conductive hearing loss or sensorineural hearing loss. The sensorineural hearing loss can be the hearing loss caused by noise, drugs, aging, trauma and viruses, and particularly, can be ototoxic hearing loss. The ototoxic hearing loss can be the hearing loss caused by the administration of any one or more ototoxic medications selected from the group consisting of gentamycin, streptomycin, kanamycin, neomycin, amikacin, tobramycin, netilmicin, dibekacin, sisomycin, livodomycin, cisplatin, carboplatin and oxaliplatin.

Figure 1:
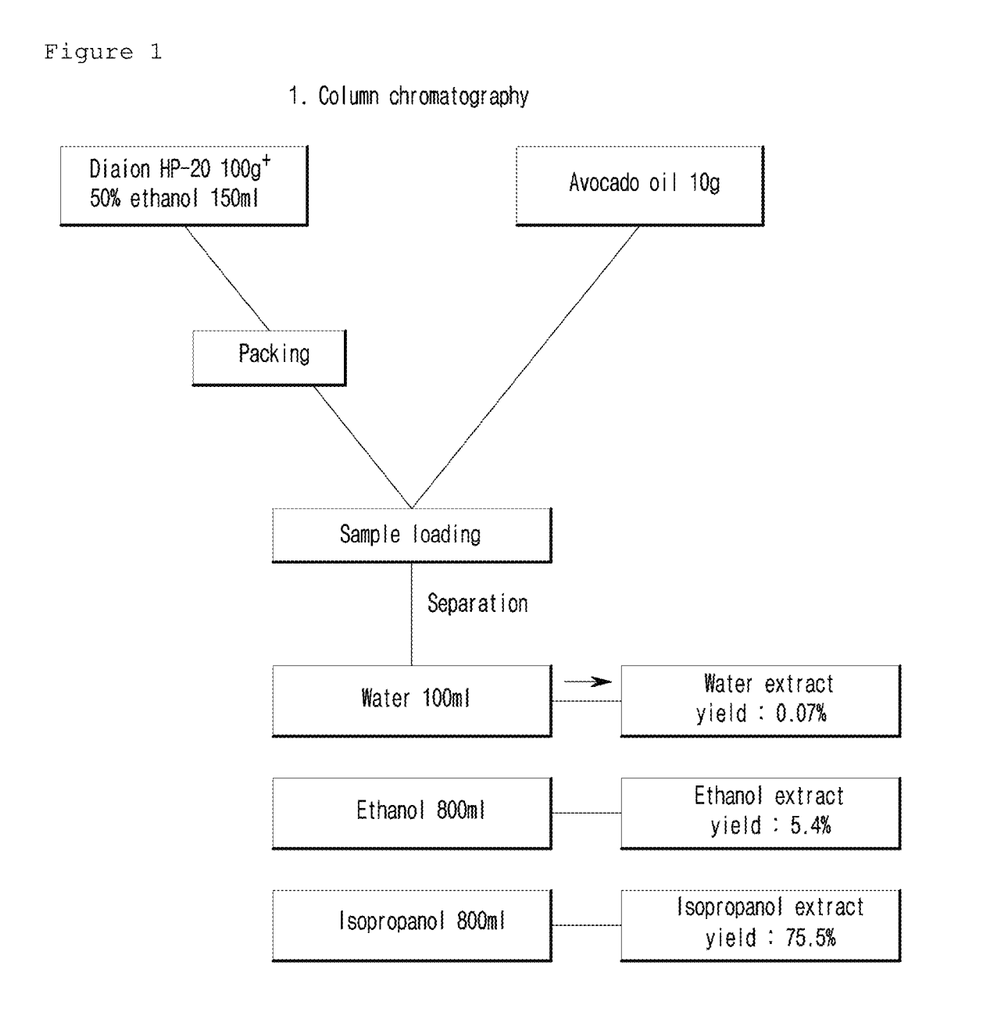
FIG. 1 is a schematic diagram illustrating the process of preparing a fraction of water, ethanol or isopropanol by performing adsorption chromatography using avocado oil.

In a preferred embodiment of the present invention, the inventors performed adsorption chromatography using avocado oil. Particularly, water, ethanol and isopropanol fractions of avocado oil were prepared by adsorbing avocado oil on adsorption chromatography and then sequentially adding water, ethanol and isopropanol as eluting solvents (see FIG. 1).

Figure 2:
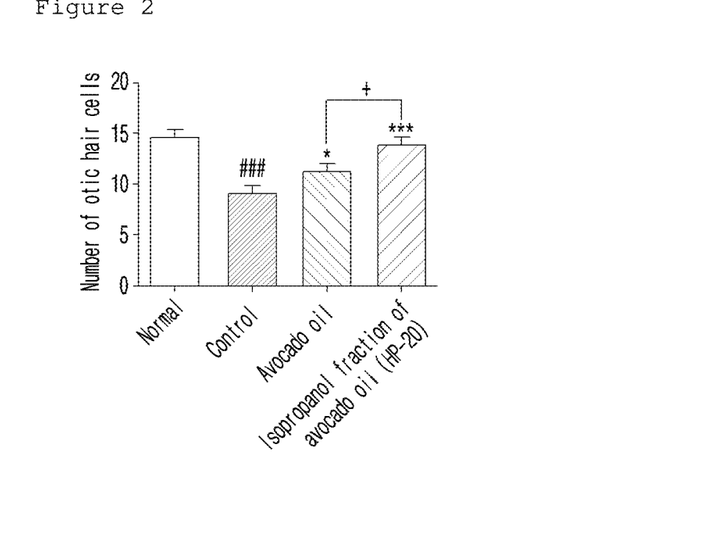
FIG. 2 is a graph illustrating that the isopropanol fraction (HP-20) of avocado oil increased the number of hair cells of zebrafish reduced by neomycin.
Figure 3:
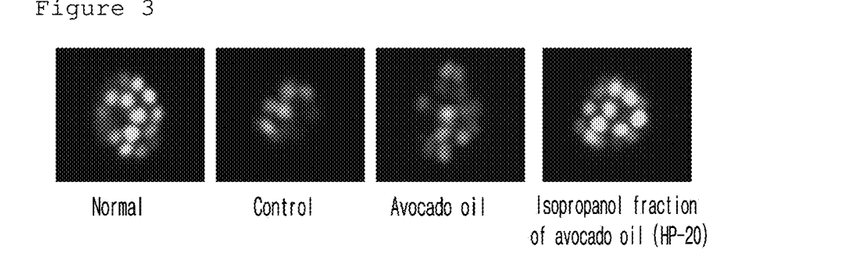
FIG. 3 is a set of photomicrographs illustrating that the isopropanol fraction (HP-20) of avocado oil increased the number of hair cells of zebrafish reduced by neomycin.

The isopropanol fraction of avocado oil prepared above significantly increased the number of hair cells reduced by neomycin in zebrafish animal models than avocado oil (see FIGS. 2 and 3).

Figure 4:
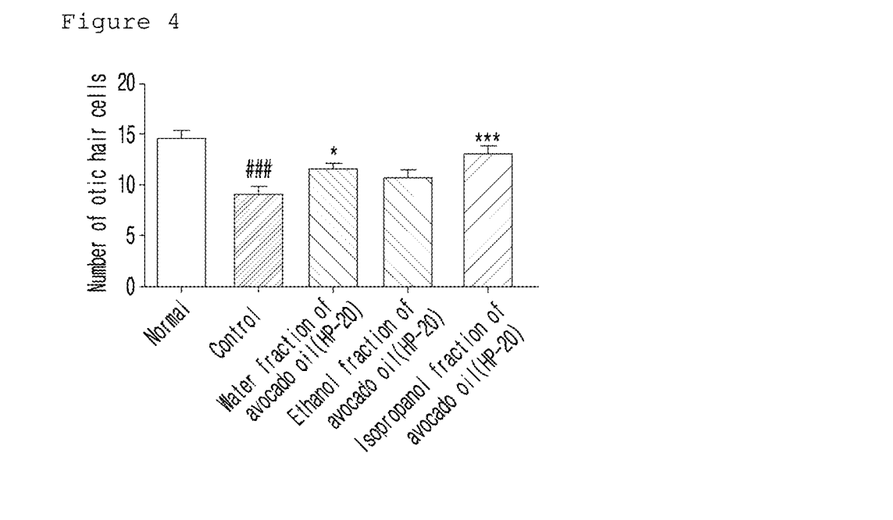
FIG. 4 is a graph illustrating that the isopropanol fraction of avocado oil increased the number of hair cells of zebrafish reduced by neomycin when treated with the fractions of water, ethanol and isopropanol (HP-20) of avocado oil, respectively.
Figure 5:
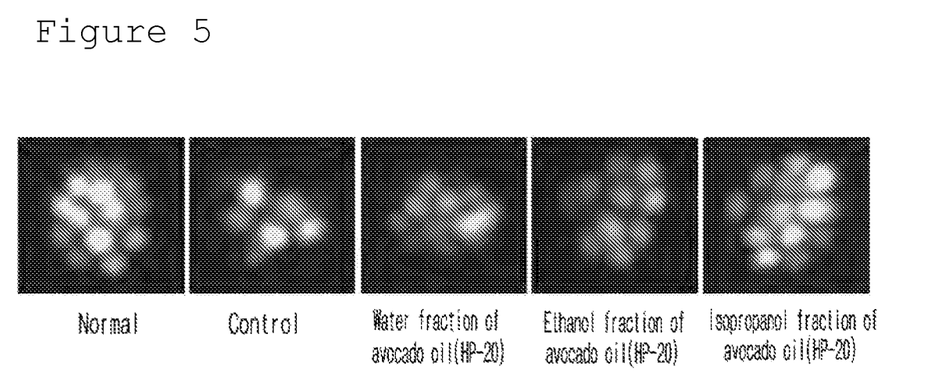
FIG. 5 is a set of photomicrographs illustrating that the isopropanol fraction of avocado oil increased the number of hair cells of zebrafish reduced by neomycin when treated with the fractions of water, ethanol and isopropanol (HP-20) of avocado oil, respectively.

The isopropanol fraction of avocado oil prepared above significantly increased the number of hair cells reduced by neomycin in zebrafish animal models than the water and ethanol fractions (see FIGS. 4 and 5).

Figure 6A:
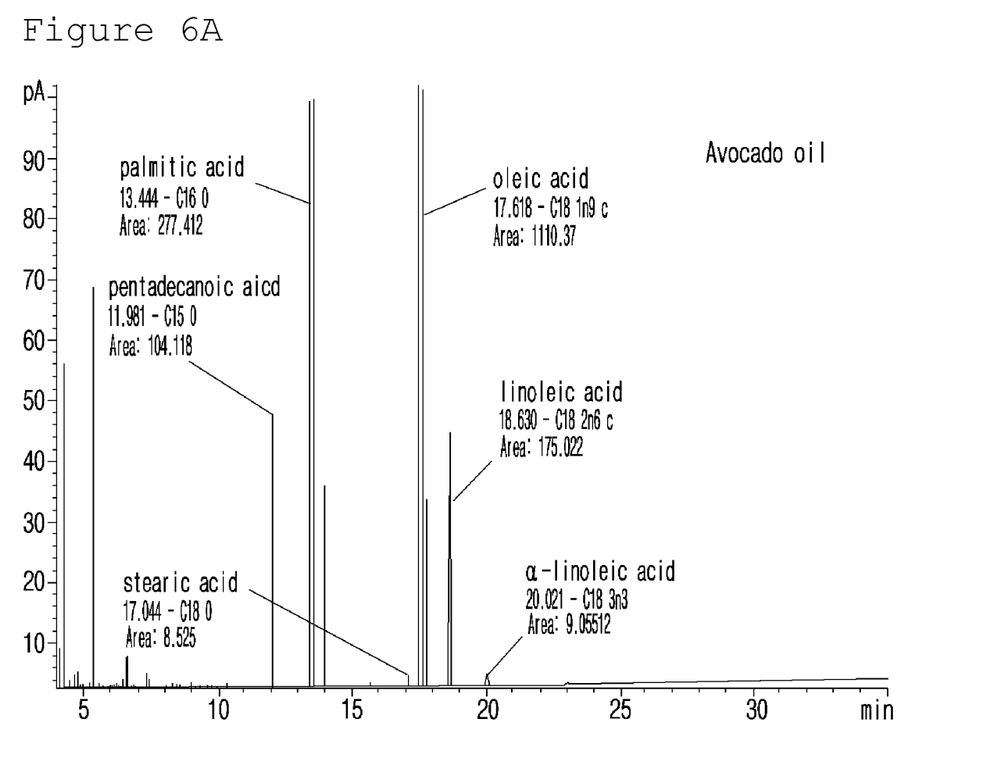
FIG. 6A is the results of analyzing the components of avocado oil (AGO).
Figure 6B:
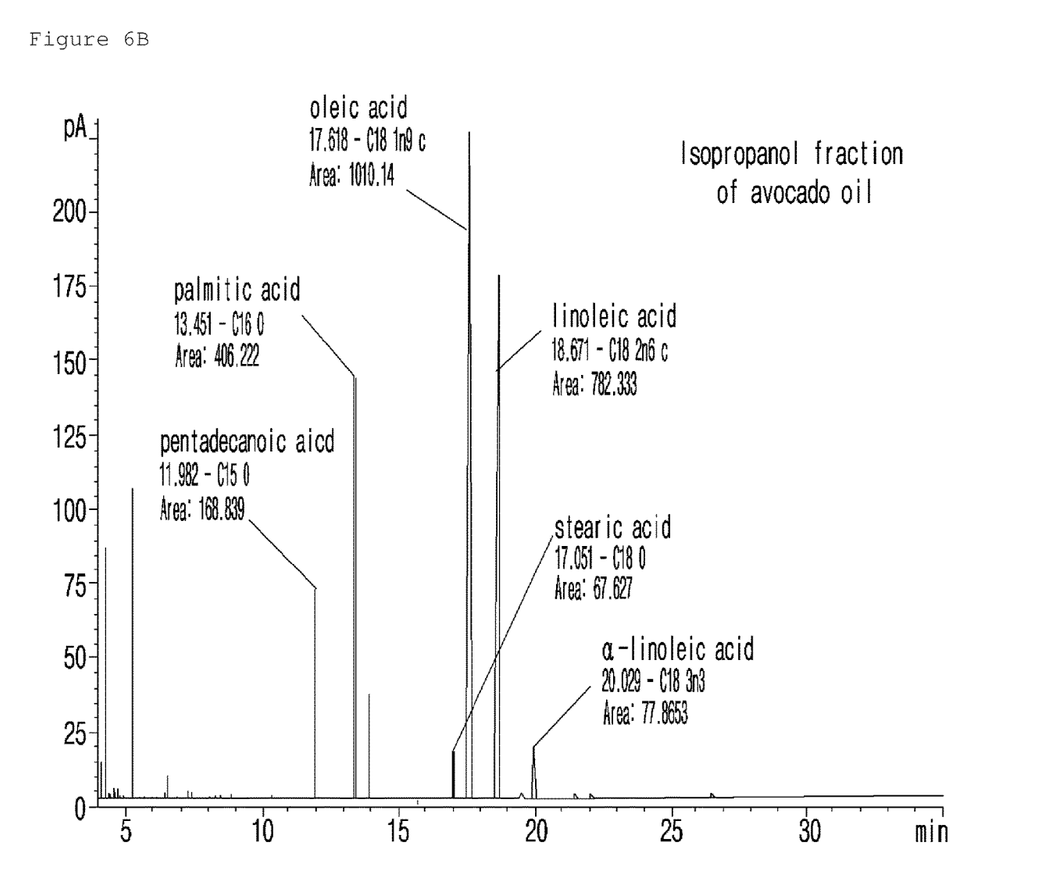
FIG. 6B is the results of analyzing the components of the isopropanol fraction (AGL) of avocado oil.
Figure 6C:
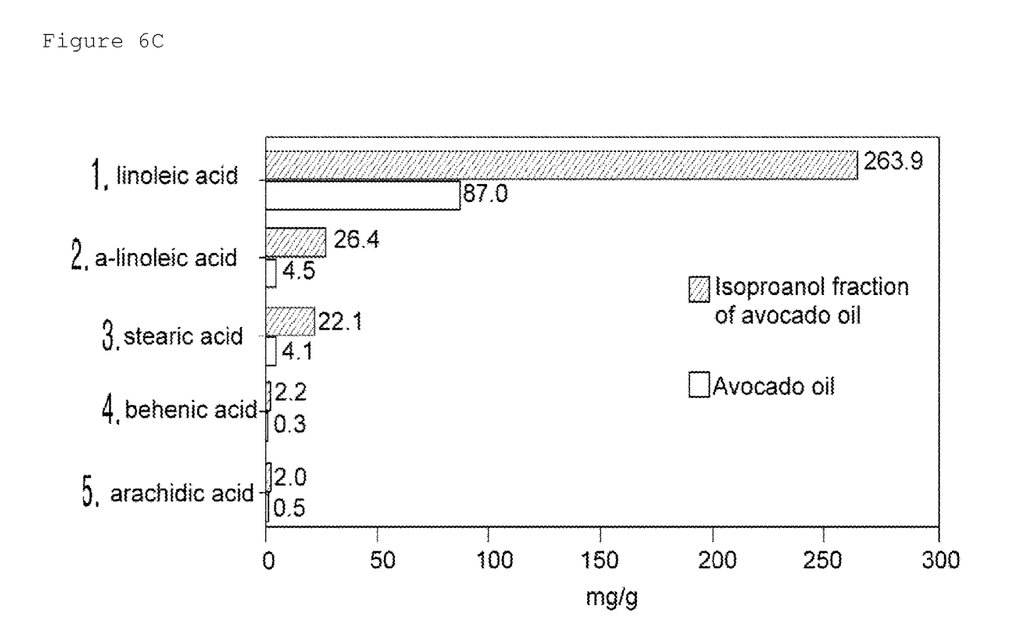
FIG. 6C is the results of comparing the content of the major components in the isopropanol fraction of avocado oil and avocado oil.

The isopropanol fraction of avocado oil prepared above showed a different composition from avocado oil, and particularly, the content of linoleic acid, alpha-linoleic acid and stearic acid was high (see FIGS. 6A to 6C).

Figure 7:
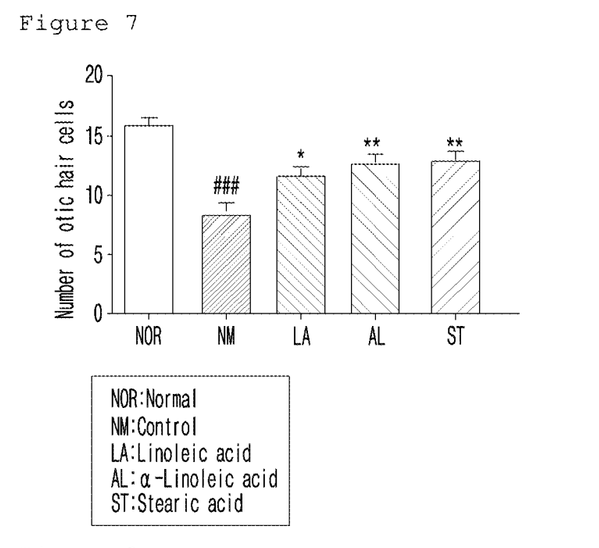
FIG. 7 is a graph illustrating that linoleic acid, alpha-linoleic acid and stearic acid in the isopropanol fraction of avocado oil increased the number of hair cells of zebrafish reduced by neomycin.
Figure 8:
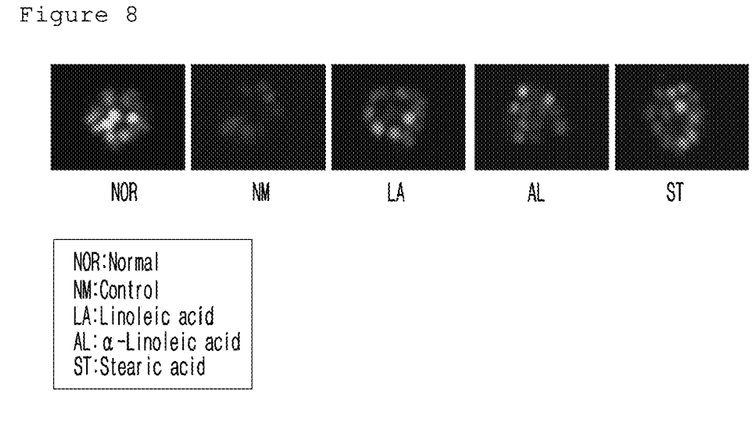
FIG. 8 is a set of photomicrographs illustrating that linoleic acid, alpha-linoleic acid and stearic acid in the isopropanol fraction of avocado oil increased the number of hair cells of zebrafish reduced by neomycin.
Figure 9A:
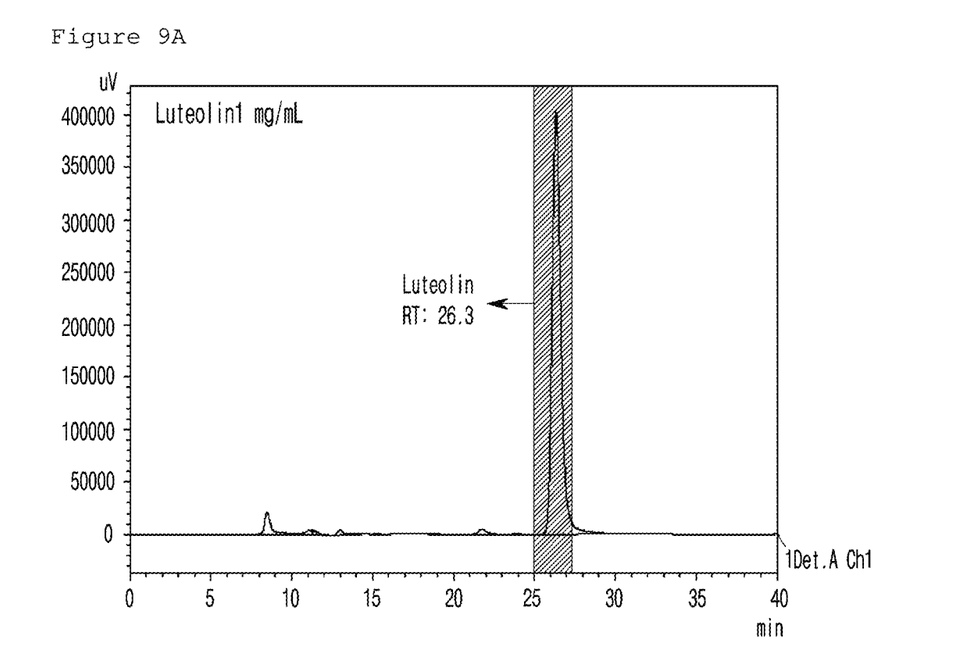
FIG. 9A is a HPLC (high-performance liquid chromatography) data of Luteolin.
Figure 9B:
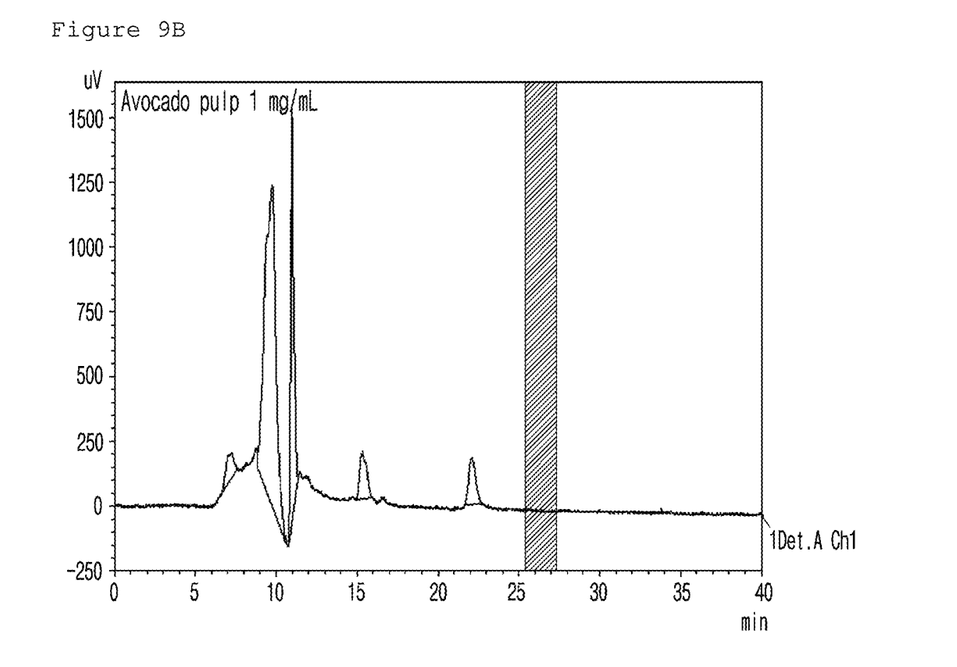
FIG. 9B is a HPLC (high-performance liquid chromatography) data of the avocado pulp.
Figure 9C:
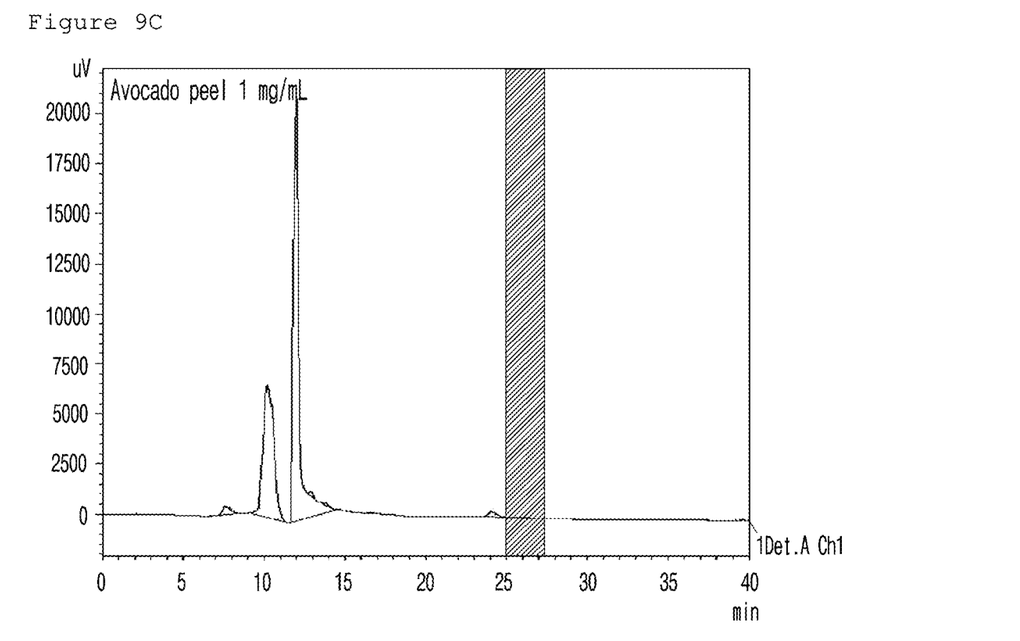
FIG. 9C is a HPLC (high-performance liquid chromatography) data of the avocado peel.
Figure 9D:
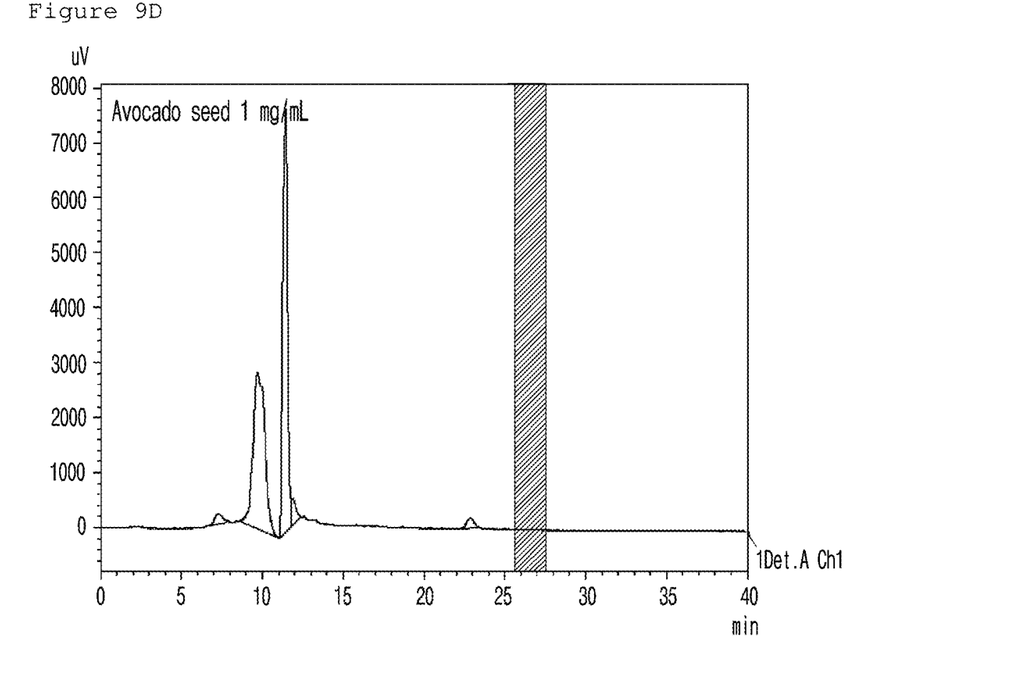
FIG. 9D is a HPLC (high-performance liquid chromatography) data of the avocado seed.

In addition, linoleic acid, alpha-linoleic acid and stearic acid in the isopropanol fraction of avocado oil significantly increased the number of hair cells reduced by neomycin in zebrafish animal models, respectively (see FIGS. 7 and 8).

Therefore, the isopropanol fraction of avocado oil of the present invention can be effectively used for the treatment of hearing loss.

The pharmaceutical composition according to the present invention can include the isopropanol fraction of avocado oil as an active ingredient by 10~95 weight % for the total weight of the composition. In addition, the pharmaceutical composition of the present invention can include, in addition to the active ingredient, one or more effective ingredients having the same or similar function to the active ingredient.

The pharmaceutical composition of the present invention can include any generally used carriers, diluents, excipients, or a mixture thereof. The pharmaceutically acceptable carrier can be any carrier that is able to deliver the composition of the present invention in the living body without limitation, which is exemplified by the compounds described in Merck Index, $13^{th}$ ed., Merck & Co. Inc., such as saline, sterilized water, Ringer's solution, dextrose solution, maltodextrin solution, glycerol, ethanol or a mixture thereof. If necessary, a general additive such as an antioxidant, a buffer, and a bacteriostatic agent can be additionally added.

When the composition is formulated, generally used fillers, extenders, binders, wetting agents, disintegrating agents, diluents such as surfactants, or excipients can be added.

The composition of the present invention can be formulated as an oral or parenteral preparation. The oral preparations can include solid and liquid formulations. The solid formulations can be tablets, pills, powders, granules, capsules or troches, and such solid formulations can be prepared by adding one or more excipients to the composition. The excipient can be starch, calcium carbonate, sucrose, lactose, gelatin or a mixture thereof. Except for the simple excipients, lubricants, for example magnesium stearate, talc, etc., can be used. The liquid formulations can be suspensions, solutions, emulsions or syrups, and the above-mentioned formulations can contain various excipients such as wetting agents, sweeteners, aromatics and preservatives.

Formulations for parenteral administration can include injections, suppositories, respiratory inhalation powders, spray aerosols, powders and creams, and the like. The injections can include sterile aqueous solutions, non-aqueous solvents, suspensions, emulsions, and the like. Non-aqueous solvents and suspensions can contain propylene glycol, polyethylene glycol, vegetable oil like olive oil, injectable ester like ethylolate, etc.

The composition of the present invention can be administered orally or parenterally according to the desired method. Parenteral administration can include intraperitoneal injection, rectal injection, subcutaneous injection, intravenous injection, intramuscular injection or intrathoracic injection.

The composition can be administered by the pharmaceutically effective amount. The effective amount can be determined according to the type of disease, the severity, the activity of the drug, the patient's sensitivity to the drug, the time of administration, the route of administration, the duration of treatment, the drugs being used simultaneously, and the like. However, for the desired effect, the amount of the active ingredient included in the pharmaceutical composition according to the present invention can be 0.0001~100 mg/kg, specifically 0.001~10 mg/kg. The administration frequency is once a day or a few times a day.

The composition of the present invention can be administered alone or in combination with other therapeutic agents. In combination administration, the administration can be sequential or simultaneous.

The present invention also provides a health functional food containing an isopropanol fraction of avocado oil as an active ingredient for the amelioration of hearing loss.

The isopropanol fraction of avocado oil according to the present invention can have the characteristics as described above. For example, the avocado oil can be the oil extracted from any one or more selected from the group consisting of peel, pulp and seeds of avocado. The fraction can be obtained by adsorbing avocado oil on a chromatography filled with a resin for adsorption chromatography, and then sequentially adding water, ethanol and isopropanol as eluting solvents.

The hearing loss is as described above. For example, the hearing loss can be conductive hearing loss or sensorineural hearing loss, and particularly, can be sensorineural hearing loss. The sensorineural hearing loss can be ototoxic hearing loss.

In a preferred embodiment of the present invention, the inventors performed adsorption chromatography using avocado oil. Particularly, water, ethanol and isopropanol fractions of avocado oil were prepared by adsorbing avocado oil on adsorption chromatography and then sequentially adding water, ethanol and isopropanol as eluting solvents (see FIG. 1).

The isopropanol fraction of avocado oil prepared above significantly increased the number of hair cells reduced by neomycin in zebrafish animal models than avocado oil (see FIGS. 2 and 3).

The isopropanol fraction of avocado oil prepared above significantly increased the number of hair cells reduced by neomycin in zebrafish animal models than the water and ethanol fractions (see FIGS. 4 and 5).

The isopropanol fraction of avocado oil prepared above showed a different composition from avocado oil, and particularly, the content of linoleic acid, alpha-linoleic acid and stearic acid was high (see FIGS. 6A to 6C).

In addition, linoleic acid, alpha-linoleic acid and stearic acid in the isopropanol fraction of avocado oil significantly increased the number of hair cells reduced by neomycin in zebrafish animal models, respectively (see FIGS. 7 and 8). Therefore, the isopropanol fraction of avocado oil can be effectively used for the amelioration of hearing loss.

The composition of the present invention can be added to food as it is or after being mixed with other food or ingredients. At this time, the content of the active ingredient added can be determined according to the purpose, and generally can be 0.01~90 weight parts for the total weight of the food.

The form and type of the health functional food are not particularly limited. Specifically, the health functional food can be in the form of tablets, capsules, powders, granules, liquids and pills. The health functional food can include various flavors, sweeteners or natural carbohydrates as additional ingredients. The sweeteners can be natural or synthetic sweeteners, and the natural sweeteners are exemplified by taumartin, stevia extract, and the like. The synthetic sweeteners are exemplified by saccharin and aspartame, etc. In addition, the natural carbohydrates can be monosaccharides, disaccharides, polysaccharides, oligosaccharides and sugar alcohols, etc.

In addition to the ingredients mentioned above, the health functional food of the present invention can include in a variety of nutrients, vitamins, minerals, flavors, coloring agents, pectic acid and its salts, alginic acid and its salts, organic acids, protective colloidal viscosifiers, pH regulators, stabilizers, antiseptics, glycerin, alcohols, etc. All the mentioned ingredients can be added singly or together. The mixing ratio of those ingredients does not matter in fact, but in general, each can be added by 0.01~0.1 weight part per 100 weight part of the composition of the present invention.

The present invention also provides a method for preventing, ameliorating or treating hearing loss, comprising the step of administering an isopropanol fraction of avocado oil to a subject.

The isopropanol fraction of avocado oil according to the present invention can have the characteristics as described above. For example, the avocado oil can be the oil extracted from any one or more selected from the group consisting of peel, pulp and seeds of avocado. The fraction can be obtained by adsorbing avocado oil on a chromatography filled with a resin for adsorption chromatography, and then sequentially adding water, ethanol and isopropanol as eluting solvents.

The said subject can be a mammal, specifically a human.

The isopropanol fraction of avocado oil of the present invention can be administered orally or parenterally according to the desired method. Parenteral administration can include intraperitoneal injection, rectal injection, subcutaneous injection, intravenous injection, intramuscular injection or intrathoracic injection.

The isopropanol fraction of avocado oil can be administered by the pharmaceutically effective amount. The effective amount can be determined according to the type of disease, the severity, the activity of the drug, the patient's sensitivity to the drug, the time of administration, the route of administration, the duration of treatment, the drugs being used simultaneously, and the like. However, for the desired effect, the amount of the active ingredient included in the isopropanol fraction of avocado oil according to the present invention can be 0.0001~100 mg/kg, specifically 0.001~10 mg/kg. The administration frequency is once a day or a few times a day.

The isopropanol fraction of avocado oil of the present invention can be administered alone or in combination with other therapeutic agents. In combination administration, the administration can be sequential or simultaneous.

In addition, the present invention provides a use of the isopropanol fraction of avocado oil for the preparation of a medicament for the prevention, amelioration or treatment of hearing loss.

The isopropanol fraction of avocado oil according to the present invention can have the characteristics as described above.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of Avocado Oil Fraction

Water, ethanol or isopropanol fraction of avocado oil was prepared by performing adsorption chromatography using avocado oil.

Particularly, 100 g of Diaion HP-20 resin was added to 150 ml of 50% (v/v) ethanol, which was filled in a column. Meanwhile, 10 g of avocado oil purchased from Avoplus (Diricom), Mexico was diluted to 50% (w/v) in 50% (v/v) ethanol, which was loaded on the prepared column. The avocado oil purchased from Mexico was prepared by oil-pressing the peel and pulp of avocado. Water fraction was obtained by adding 100 ml of water to the column loaded with avocado oil. Then, ethanol fraction was obtained by adding 800 ml of 99% (v/v) ethanol thereto, and isopropanol fraction (HP-20) was obtained by adding 800 ml of isopropanol. When obtaining the water, ethanol or isopropanol fraction, each eluting solvent was used by heating to a temperature of 60 to 70° C.

At this time, yield of the water fraction of avocado oil was 0.07%, yield of the ethanol fraction was 5.4%, and yield of the isopropanol fraction was 75.5%.

EXPERIMENTAL EXAMPLE 1

Confirmation of Effect of Avocado Oil Fraction on Ototoxicity—(1)

The effect of the isopropanol fraction of avocado oil prepared in Example 1 on hair cells reduced by neomycin was confirmed by the following method.

Particularly, 6 days after fertilization, zebrafish larvaes were placed in 24-well plates and neomycin was added thereto at the concentration of 1 μM. One hour later, neomycin was removed and the isopropanol fraction of avocado oil prepared in Example 1 was added at the concentration of 1 μg/ml. At this time, avocado oil was used as the control and 0.03% (w/v) sea salt solution was used as the untreated control. Twelve hours later, 0.1% YO-PRO (Life Technologies, USA) was added to stain hair cells of the larvaes for 30 minutes. The stained hair cells were observed using a fluorescence microscope (Olympus 1x70, Olympus, Japan), and the number thereof was shown in FIG. 2. In addition, photomicrographs of hair cells were shown in FIG. 3.

As shown in FIG. 2 and FIG. 3, the number of hair cells was significantly increased in the larvaes added with the isopropanol fraction of avocado oil, compared to avocado oil (FIGS. 2 and 3).

EXPERIMENTAL EXAMPLE 2

Confirmation of Effect of Avocado Oil Fraction on Ototoxicity—(2)

The effect of the water, ethanol and isopropanol fractions of avocado oil prepared in Example 1 on hair cells reduced by neomycin was confirmed by the following method.

Water, ethanol and isopropanol fractions of avocado oil were added to the zebrafish larvaes, respectively, instead of adding the isopropanol fraction of avocado oil, and the number of hair cells stained by the same manner described in Experimental Example 1 was counted and shown in FIG. 4. In addition, photomicrographs of the hair cells taken with a fluorescence microscope were shown in FIG. 5.

As shown in FIG. 4 and FIG. 5, the number of hair cells was significantly increased in the larvaes added with the isopropanol fraction of avocado oil, compared to the water and ethanol fractions of avocado oil (FIGS. 4 and 5).

EXPERIMENTAL EXAMPLE 3

Comparison of Components of Avocado Oil Fraction

The components of avocado oil and the isopropanol fraction of avocado oil prepared in Example 1 were analyzed by GC-MS.

As a result, it was confirmed that the specific components were significantly higher in the isopropanol fraction of avocado oil than avocado oil (FIGS. 6A~6C). Five components with significantly higher content in the isopropanol fraction of avocado oil than in avocado oil were derived. And the top three components were tested for efficacy on ototoxicity.

EXPERIMENTAL EXAMPLE 4

Confirmation of Effect of Single Substance in Avocado Isopropanol Fraction on Ototoxicity The effect of linoleic acid, alpha-linolenic acid and stearic acid, the components identified as high in the isopropanol fraction of avocado oil in Experimental Example 3, on hair cells reduced by neomycin was confirmed by the following method.

Instead of adding the isopropanol fraction of avocado oil, 1 μg/ml of linoleic acid, alpha-linolenic acid and stearic acid were added to the zebrafish larvaes, respectively, and the number of hair cells stained by the same manner described in Experimental Example 1 was counted and shown in FIG. 7. In addition, photomicrographs of the hair cells taken with a fluorescence microscope were shown in FIG. 8.

As shown in FIG. 7 and FIG. 8, the number of hair cells was significantly increased in the larvaes added with linoleic acid, alpha-linolenic acid and stearic acid (FIGS. 7 and 8).

EXPERIMENTAL EXAMPLE 5

Analysis of Whether Avocados Contain Luteolin (HPLC)

JP 2011-037738 (Feb. 24, 2011) describes an experiment to confirm the resistance to hearing loss of "Luteolin". So to determine whether avocado contains luteolin, the avocado extract (peel, pulp, seed) was analyzed by HPLC (high-performance liquid chromatography).

[HPLC Condition]
Column: c18 (4.6×250 mm, 5 um)
Mobile phase:
A: 0.05% phosphoric acid in water (60%)
B: acetonitrile (40%)
Flow rate: 1 mL/min
Detector: UV 330 nm As shown in FIGS. 9A to 9D, all of the extract of peel, pulp and seed of avocado did not show any peaks corresponding to luteolin. This shows that avocado do not contain luteolin.

EXPERIMENTAL EXAMPLE 6

Confirmation of Effect of Avocado Oil, Isopropanol Fraction of Avocado Oil and Avocado Extract on Ototoxicity Preparation of Avocado Peel+Pulp Oil (A)

Avocado (product in Mexico) was peeled and 612.1 g of the peel was obtained. The obtained peel were dried at 55° C. for 48 hours, by which 138.5 g of the dried avocado peel was obtained. Avocado peel oil was prepared from the dried avocado peel using an expeller oil press (Oil Love Premium L Wrench Automatic, NATIONAL ENG CO., LTD) at 55° C. The prepared avocado peel oil was centrifuged at 20° C. at 12,000 rpm, and the supernatant was filtered to obtain 70.8 g of the avocado peel oil to be used in the experiment in the yield of 11.56%. The prepared avocado peel oil was stored at room temperature until use.

Avocado Oil (B)

10 g of avocado oil which was purchased from Avoplus (Diricom), Mexico, was prepared.

Avocado Oil Isopropanol Fraction (C)

The isopropanol fraction of avocado oil prepared in Example 1 was prepared.

Preparation of Avocado Butylene Glycol Extract (D)

300 g of dried avocado pulp was obtained by drying 1105 g of avocado (product in Mexico) pulp at 55° C. for 48 hours. 500 ml of butylene glycol was added to the dried avocado pulp, and then the butylene glycol extract of avocado pulp was prepared using a 40 kHz ultrasonic extractor at 55° C. for 1 hour. The obtained extract was filtered and concentrated to give 82.5 g of the butylene glycol extract of avocado pulp in the yield of 7.46%.

Preparation of Avocado Ethanol, Butylene Glycol Extract (E)

302 g of dried avocado pulp was obtained by drying 1105 g of avocado (product in Mexico) pulp at 55° C. for 48 hours. 250 ml of ethanol was added to the dried avocado pulp, and the ethanol extract of avocado pulp was prepared using a 40 kHz ultrasonic extractor at 55° C. for 1 hour. Then, the ethanol & butylene glycol extract was prepared by adding 250 ml of butylene glycol thereto. The obtained extract was filtered and concentrated to give 85.2 g of the butylene glycol extract of avocado pulp in the yield of 7.71%.

Confirmation of Effect of Isopropanol Fraction of Avocado Oil on Ototoxicity

The effect of A-E prepared above on hair cells reduced by neomycin was confirmed by the following method.

Particularly, 6 days after fertilization, zebrafish larvaes were placed in 24-well plates and neomycin was added thereto at the concentration of 1 μM. One hour later, neomycin was removed and A-E were added at the concentration of 10 μg/ml. At this time, 0.03% (w/v) sea salt solution was used as the control. Twelve hours later, 0.1% YO-PRO (Life Technologies, USA) was added to stain hair cells of the larvaes for 30 minutes. The stained hair cells were observed using a fluorescence microscope (Olympus 1x70, Olympus, Japan), and the number of the observed hair cells was counted and analyzed. As a result, the number of hair cells observed with a fluorescence microscope was shown in FIG. 10.

Figure 10:
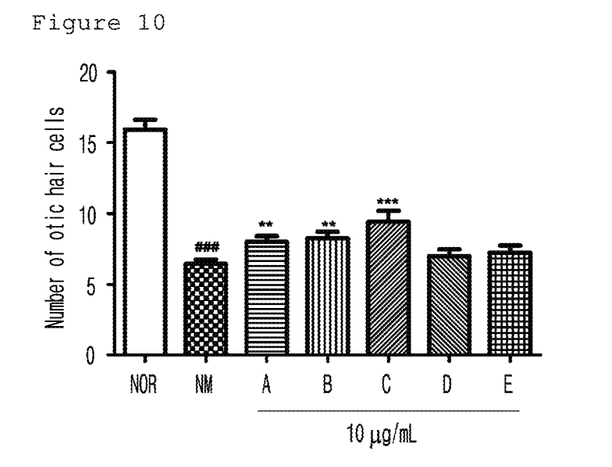
FIG. 10 is a graph illustrating that the treatment of avocado oil of peel+pulp (A), avocado oil (B), isopropanol fraction of avocado oil (C), avocado butylene glycol extract (D) and avocado ethanol, butylene glycol extract (E) increased the number of hair cells of zebrafish reduced by neomycin.

As shown in FIG. 10, the number of hair cells was significantly increased in the larvaes added with avocado oil and the isopropanol fraction of avocado oil (FIG. 10).

EXPERIMENTAL EXAMPLE 7

Confirmation of Effect of Isopropanol Fraction of Avocado Oil and Avocado Butylene Glycol Extract Preparation of Isopropanol Fraction of Avocado Oil (IPA) and Avocado Butylene Glycol Extract (BG)

IPA and BG were the same as the isopropanol fraction of avocado oil (C) and avocado butylene glycol extract D) prepared in the Experimental Example 6.

Confirmation of Effect of Isopropanol Fraction of Avocado Oil on Ototoxicity

The effect of IPG and BG prepared above on hair cells reduced by kanamycin was confirmed by the following method.

Particularly, 6 days after fertilization, zebrafish larvaes were placed in 24-well plates and kanamycin was added thereto at the concentration of 1 μM. One hour later, kanamycin was removed and IPG and BG were added at the concentration of 10 μg/ml. At this time, 0.03% (w/v) sea salt solution was used as the control. Twelve hours later, 0.1% YO-PRO (Life Technologies, USA) was added to stain hair cells of the larvaes for 30 minutes. The stained hair cells were observed using a fluorescence microscope (Olympus 1x70, Olympus, Japan), and the number of the observed hair cells was counted and analyzed. As a result, the number of hair cells observed with a fluorescence microscope was shown in FIG. 11 and photomicrographs of the hair cells taken with a fluorescence microscope were shown in FIG. 12.

Comprising this Experimental Example 7 and the above Experimental Example 6 conditions, it can be seen that kanamycin is more toxic than neomycin, which further reduces the number of hair cells of zebrafish fry treated with kanamycin.

Figure 11:
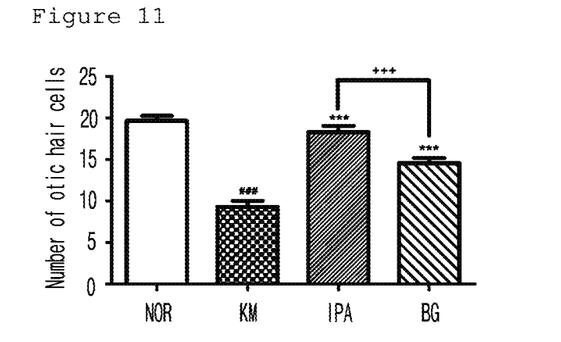
FIG. 11 is a graph illustrating that the treatment of isopropanol fraction of avocado oil (IPA) and avocado butylene glycol extract (BG) increased the number of hair cells of zebrafish reduced by kanamycin.
Figure 12:
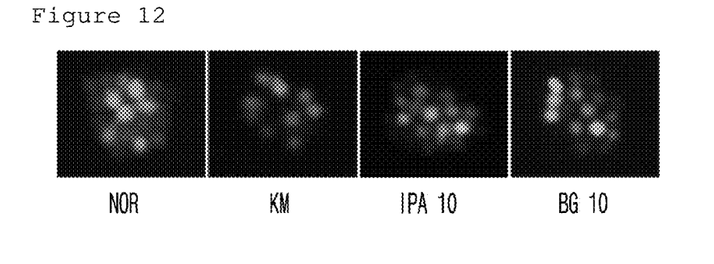
FIG. 12 is a set of photomicrographs illustrating that the isopropanol fraction of avocado oil increased the number of hair cells of zebrafish reduced by kanamycin.

As shown in FIG. 11 and FIG. 12, the number of hair cells was significantly increased in the larvaes added with the isopropanol fraction of avocado oil (IPA) (FIG. 11 and FIG. 12).

EXPERIMENTAL EXAMPLE 8

Fatty Acid Content Analysis of Avocado Butylene Glycol Extract (GC)

In Experimental Example 3 of the present invention, we confirmed the five substances having a significantly high component content in isopropanol fraction of avocado oil than avocado oil, and in Experimental Example 4, the effect on the endotoxin was confirmed for the three substances (fatty acid). Therefore, the present inventors confirmed the fatty acid content of avocado butylene glycol by analyzing each component of the isopropanol fraction of avocado oil and the avocado butylene glycol extract through gas chromatography (GC).

Figure 13:
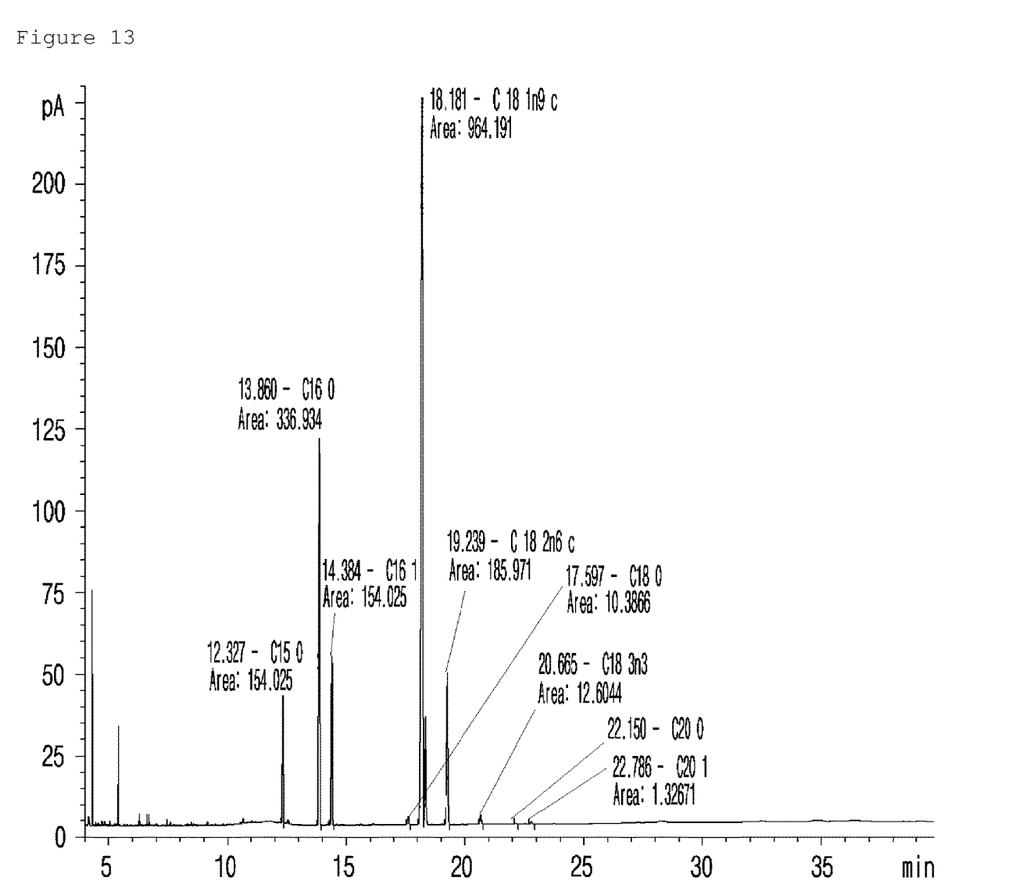
FIG. 13 is the result of analyzing the component of the isopropanol fraction of avocado oil (IPA) by GC (Gas chromatography).
Figure 14:
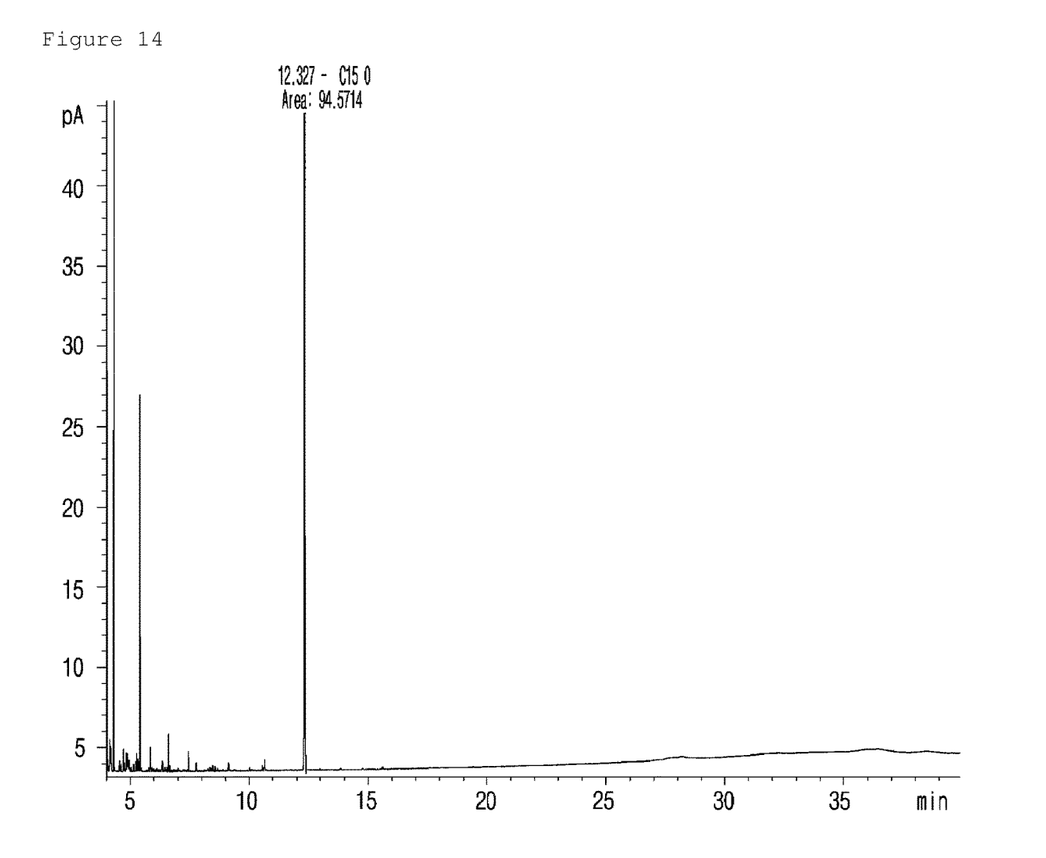
FIG. 14 is the result of analyzing the component of the avocado butylene glycol extract (BG) by GC (Gas chromatography).

The results are shown in the table 1 and FIG. 13 and FIG. 14.

TABLE 1

| | Butyric acid(C4) | Caproic acid(C6) | Caprylic acid(C8) | Capric acid(C10) | Undecylic acid(C11) | Lauric acid(C12) | Tridecylic acid(C13) |
|---|---|---|---|---|---|---|---|
| IPA | — | — | — | — | — | — | — |
| BG | — | — | — | — | — | — | — |

| | Myristic acid(C14) | Myristoleic acid(C14) | Cis-10-Pentadecenoic acid(C15) | Palmitic acid(C16) | Palmitoleic acid(C16) | Margaric acid(C17) | cis-10-heptadecenoic acid(C17) |
|---|---|---|---|---|---|---|---|
| IPA | — | — | — | 164.627 | 76.658 | — | — |
| BG | — | — | — | — | — | — | — |

| | Stearic acid(C18) | Elaidic acid(C18) | Oleic acid(C18) | Linolelaidic acid(C18) | Linoleic acid(C18) | Gamma-linolenic acid(C18) | Alpha-linolenic acid(C18) |
|---|---|---|---|---|---|---|---|
| IPA | 4.916 | — | 458.183 | — | 91.661 | — | 6.384 |
| BG | — | — | — | — | — | — | — |

| | Arachidic acid(C20) | Eicosenoic acid(C20) | Eicosadienoic acid(C20) | Dihomo-gamma-linolen acid(C20) | Heneicosylic acid(C21) | Arachidonic acid(C20) | Eicosa-trienoic acid(C20) |
|---|---|---|---|---|---|---|---|
| IPA | 0.616 | 1.640 | — | — | — | — | — |
| BG | — | — | — | — | — | — | — |

| | Eicosa-pentaenoic acid(C20) | Behenic acid(C22) | Erucic acid(C22) | Docosa-dienoic acid(C22) | Tricosylic acid(C23) | Lignoceric acid(C24) | Docosa-hexaenoic acid(C22) | Nervonic acid(C24) |
|---|---|---|---|---|---|---|---|---|
| IPA | — | — | — | — | — | — | — | — |
| BG | — | — | — | — | — | — | — | — |

(mg/g)

As shown in FIG. 13 and FIG. 14, The isopropanol fraction of avocado oil was found to contain a large amount of fatty acids such as palmitic acid, palmitoleic acid, oleic acid, and linoleic acid, but the avocado butylene glycol extract contained little fatty acid.

What is claimed is:

1. A method for preventing, ameliorating or treating hearing loss, comprising
   administering a pharmaceutically effective amount of an isopropanol fraction of avocado oil to a subject, wherein the isopropanol fraction is obtained by:

adsorbing avocado oil on adsorption chromatography; and adding water, ethanol and isopropanol sequentially as eluting solvents, thereby preventing, ameliorating or treating hearing loss in the subject.

2. The method for preventing, ameliorating or treating hearing loss according to claim 1, wherein the adsorption chromatography is performed with a column filled with silica gel or a synthetic adsorbent as a resin.

3. The method for preventing, ameliorating or treating hearing loss according to claim 1, wherein the avocado oil comprises avocado oil extracted from avocado peel, avocado pulp and/or avocado seeds.

4. The method for preventing, ameliorating or treating hearing loss according to claim 1, wherein the hearing loss is conductive hearing loss or sensorineural hearing loss.

* * * * *